United States Patent
Esmaeili (10) Patent No.: US 6,499,319 B1
(45) Date of Patent: Dec. 31, 2002

(54) TEMPERATURE CONTROL BY MEANS OF A CCD-CAMERA IN WELDING FIBER RIBBON CABLES

(75) Inventor: Sasan Esmaeili, Solna (SE)

(73) Assignee: Telefonaktiebolaget LM Ericsson, Stockholm (SE)

( * ) Notice: Subject to any disclaimer, the term of this patent is extended or adjusted under 35 U.S.C. 154(b) by 0 days.

(21) Appl. No.: 09/584,472

(22) Filed: Jun. 1, 2000

Related U.S. Application Data (62) Division of application No. 09/023,300, filed on Feb. 13, 1998, now Pat. No. 6,097,426.

(30) Foreign Application Priority Data

Feb. 14, 1997 (SE) ............................................... 9700534

(51) Int. Cl.⁷ ............................................. C03B 37/07
(52) U.S. Cl. ............................. 65/484; 65/501; 65/488
(58) Field of Search ........................ 65/501, 407, 484, 65/488

(56) References Cited

U.S. PATENT DOCUMENTS

| | | | |
|---|---|---|---|
| 4,049,414 A | | 9/1977 | Smith |
| 4,326,870 A | * | 4/1982 | Bendit ........................ 65/407 |
| 4,383,844 A | * | 5/1983 | Kashima ...................... 65/501 |
| 4,654,065 A | * | 3/1987 | Naumann |
| 4,695,306 A | * | 9/1987 | Hakoun ....................... 65/407 |
| 4,715,876 A | * | 12/1987 | Osaka ......................... 65/501 |
| 4,725,297 A | * | 2/1988 | Grigsby ....................... 65/501 |
| 4,945,776 A | * | 8/1990 | Yamada et al. ............. 356/73.1 |
| 4,978,201 A | * | 12/1990 | Yamada et al. ................ 385/96 |
| 5,009,513 A | * | 4/1991 | Onodera et al. ............. 156/158 |
| 5,218,184 A | * | 6/1993 | Hakoun ....................... 65/407 |
| 5,257,337 A | * | 10/1993 | Grigsby et al. ........ 219/121.12 |
| 5,417,733 A | * | 5/1995 | Wesson ........................ 65/407 |
| 5,648,007 A | * | 7/1997 | Reslingen .................... 65/407 |
| 5,951,735 A | * | 9/1999 | Ruegenberg ................. 65/407 |

FOREIGN PATENT DOCUMENTS

| | | | | |
|---|---|---|---|---|
| JP | 53-39143 | * | 4/1978 | .................. 65/407 |
| JP | 2-28605 | | 1/1990 | |
| JP | 2-129607 | | 5/1990 | |
| JP | 5-142442 | | 6/1993 | |

OTHER PUBLICATIONS

Toda, Y. et al, Optical Fiber Cutting Tool and Automatic Splicing Machine, Sumitomo Electric Technical Review, Nubber 19, Jan. 1980 pp85–91.*

Kiss, G. et al., "High Yield Fusion Splicing in the Outside Plant: Using Fiber Meltback to Monitor Electrode Condition", National Fiber Operation Engineering Converence, Denver, USA, Sep., 1996, pp 819–835.

* cited by examiner

*Primary Examiner*—John Hoffmann
(74) *Attorney, Agent, or Firm*—Burns, Doane, Swecker & Mathis, L.L.P.

(57) ABSTRACT

In welding optical fiber ribbons by means of an electric arc formed between electrodes the region heated by the electric arc is mapped on CCD-elements in a camera. In the obtained picture the light intensity of those portions of the picture is determined which correspond to the heated fiber portions. This light intensity is used for setting the electric current flowing between the electrodes, so that a desired welding temperature is obtained and so that also a desired, lower temperature is obtained in the fiber ends in a preparatory softening stage, which has a long durability and which is performed before the very welding stage. This determination of temperatures by means of measured light intensities gives reliable values also in the case where ambient conditions like the air pressure are changed, the state of the electrodes is changed owing to contamination, etc. During the preparatory stage the ends of the individual fibers are deformed, so that they can come in contact with each other, even if the end surfaces of the individual fibers in a fiber ribbon are not located in a plane, which extends in an angle that is exactly perpendicular to the longitudinal direction of the fiber ribbon, and so that mechanical stresses obtained when pressing the fiber ends against each other are relieved.

5 Claims, 5 Drawing Sheets

TEMPERATURE CONTROL BY MEANS OF A CCD-CAMERA IN WELDING FIBER RIBBON CABLES

This application is a divisional of Application Ser. No. 09/023,300 filed Feb. 13, 1998, now U.S. Pat. No. 6,097,426.

The present invention relates to control of temperature by means of a CCD-camera when welding optical fibers, in particular optical fiber ribbons and devices for accomplishing such control, and it also relates to a method and a device adapted to weld fiber ribbons to each other.

BACKGROUND

A very important parameter when splicing optical fibers by welding is the temperature at the welding location. To be able to maintain the temperature of the fibers at a sufficiently high level and during a sufficient long time period are determining factors in order to obtain a low attenuation and a high mechanic strength in the splice produced.

A known method for an indirect control of the temperature of the fibers, which is used in some known welding devices, is called "Meltback", see the article by G. Kiss, "High yield fusion splicing in the outside plant: using fiber meltback to monitor electrode condition", National Fiber Operation Engineering Conference, Denver, USA, September 1996.

In Patent Abstracts of Japan, abstract of the Japanese patent application No. 2129607, a fusion splicing device is disclosed, in which the brightness of an optical fiber heated in an arc discharge is observed. The discharge heating temperature is checked from the area of the bright part of the optical fiber.

When optical fibers assembled to optical fiber ribbons are to be spliced by melting the ends of the optical fibers in an electric arc, a problem exists of making the ends of the opposite individual fibers contact each other before and/or in the very fusioning process. This is due to the fact that it is very difficult to cut off such fiber ribbons at an exactly straight angle in relation to the longitudinal direction of the respective fiber ribbon. Also, the operation of stripping the polymer protective coating of a fiber ribbon and the force then used can result in that some fibers in a fiber ribbon will be elongated more than other fibers. Hence, the end surfaces of the fiber ribbon will not even be located in a plane.

In Patent Abstracts of Japan, abstract of the Japanese patent application No. 5-142442, a fusion splicing method for "multiple fibers" is disclosed, in which the connecting ends of optical fibers are preheated "at a low temperature to the extent of not attaining an excess molten state. The molten end faces of the optical fibers are then pressed to each other and while the end faces are heated in the state at the temp. higher than the above-mentioned preheating temp., the optical fibers are pushed in, by which the optical fibers are fusion spliced."

SUMMARY

It is an object of the invention to provide methods and devices for temperature control in welding optical fibers, which only use devices existing in conventional automatic welding machines, and in particular to provide methods for a simple determination of a suitable welding temperature.

It is another object of the invention to provide a method and a device which in a secure way can accomplish welded splices of fiber ribbons.

Thus the optical system and the CCD-camera, which is arranged in conventional automatic welding devices, are used for determining the light intensity in a picture of the optical fiber, when it is heated, a locked control of the CCD-camera being used, so that the automatic light intensity setting system thereof is shut off.

The light intensity in a picture captured of heated optical fibers is directly related to the fiber temperature according to Planck's radiation law. It is used for an active control of the fiber temperature in the procedure and when in advance determining suitable welding currents.

The method makes it possible for the welding device and the user to compensate for the influence of some environmental factors such as under-atmospheric pressures and electrode condition, which often cause a lowering of the temperature during the welding process, when welding parameters are used which are programmed for normal situations.

When welding optical fibers to each other, which can be optical fibers assembled to optical fiber ribbons, the following steps are used:

a. The optical fibers are heated to a welding temperature by means of an electric arc between electrodes, between which an earlier determined electrode current passes. The electrode current has here preferably been determined to always give a not to high temperature suited for welding the fibers.

b. The intensity of light emitted by the heated optical fibers is determined and is compared to a predetermined set value.

c. Thereupon, in the case where the intensity of the emitted light has been determined to deviate from the desired value by more than a predetermined amount, the electrode current is changed, preferably increased by a predetermined step, whereby the temperature of the optical fibers is also changed by a corresponding step, and thereupon the steps b. and c. are again repeated, and in the case, where the intensity of the emitted light has been determined to deviate from the set value by less than the predetermined amount, the heating is allowed to continue at this electrode current, whereby the welding is made.

A similar procedure is as follows:

a. The optical fibers are first heated to a temperature, at which they emit visible light but which temperature is well below the temperature, at which the material of the fibers melt and at which the welding is to be made.

b. The intensity of light emitted by the heated optical fibers is determined and is compared to a predetermined set value.

c. Thereupon, in the case where the intensity of the emitted light has been determined to be less than the set value, the temperature of the optical fibers is increased by a predetermined step, and thereupon steps b. and c. are again performed, and in the case where the intensity of the emitted light has been determined to be greater than or equal to the set value or to deviate from the set value by less than some small, predetermined value, the welding is made at that temperature.

A corresponding method can preferably be used for in advance determining an electrode current, which gives a desired temperature of an optical fiber, e.g. the temperature to be used in welding the fiber to a similar fiber or a temperature to be used in a softening step. The optical fiber is as above heated in an electric arc, through which an electrode current passes. The following steps are then performed:

a. An electrode current having a first value is made to pass in the electric arc in order to heat the optical fiber to a temperature, at which it emits visible light, but which is well below the desired temperature.
b. The intensity of light emitted by the heated optical fiber is determined and is compared to a predetermined set value, which is determined depending on the desired temperature.
c. Thereupon, in the case where the intensity of the emitted light has been determined to be less than the set value or generally to deviate from the set value by not less than a small, predetermined value, the electrode current is increased by a predetermined step and thereupon steps b. and c. are again performed, and in the case where the intensity of die emitted light has been determined to be equal to or higher than the set value or generally to deviate from the set value by less than the small predetermined value respectively, the used electrode current is taken as the electrode current, which gives the desired temperature. If the desired temperature is the welding temperature, the determined electrode current can then be used for welding the fiber to another fiber, whereby a correct temperature during the welding process can be achieved. The predetermined step can e.g. be equal to the small predetermined value or a little smaller.

In the step b. of the procedures described above for determining the intensity of light emitted by a heated optical fiber this determination can be made by capturing a picture of the heated optical fiber, and
analysing the picture to find values corresponding to the intensity of light only in regions of the pictures of the optical fiber corresponding to a portion of the optical fiber, which substantially corresponds to a central part of the optical fiber. The portion can have a width, as taken perpendicularly to a longitudinal direction of the optical fiber, which is substantially equal to half the diameter of the optical fiber. In the analysis the regions can be selected to be located at an end surface of the optical fiber. Further the picture can be analyzed only along lines which extend substantially perpendicularly to the longitudinal direction of the optical fiber to find the values corresponding to the light intensity. These lines are preferably located near the end surface of the optical fiber.

The procedures described above are, as has already been mentioned, particularly suited to splicing optical fiber ribbons. When splicing an end of a first optical fiber ribbon to an end of a second optical fiber ribbon by means of welding, ends of optical fibers in the first optical fiber ribbon are welded to opposite ends of optical fibers in the second optical fiber ribbon. Then the following steps can be employed:

Referring to FIGS. 7a–7e, FIG. 7a shows the first 700 and second 710 optical fiber ribbons are placed and aligned with each other, so that an end surface of an optical fiber in the first optical fiber ribbon 700 is located opposite and at an end surface of an optical fiber in the second optical fiber ribbon 710.

Figure 7A:
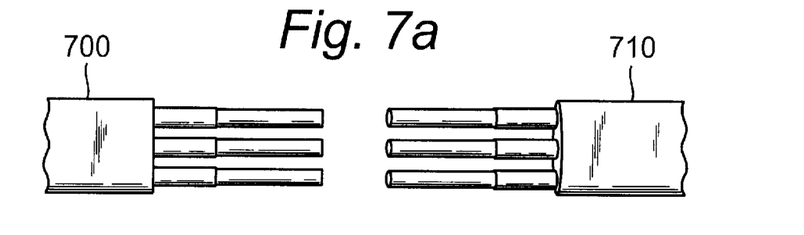
FIGS. 7a–7e depict the movement and welding process of the optical fibers in a pair of optical fiber ribbons in accordance with exemplary embodiments of the present invention.
Figure 7B:
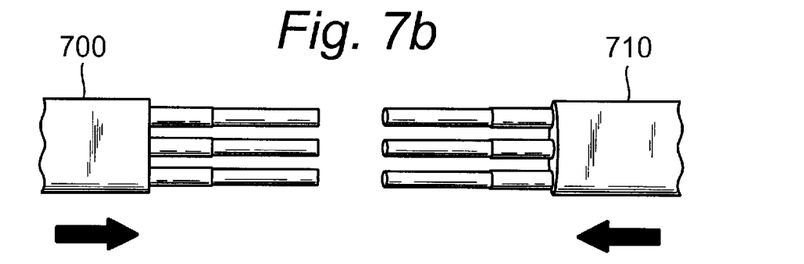
Figure 7C:
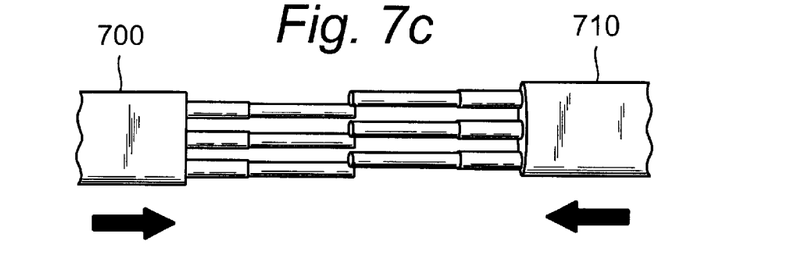
Figure 7D:
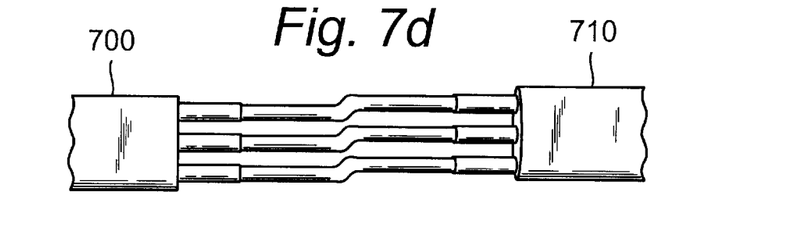

The arrows shown in FIG. 7b indicate that the end surfaces are moved in a direction to approach each other from a first position at a small distance of each other to a second position in which an end surface of at least one optical fiber in the first optical fiber ribbon 700 is in contact with an end surface of an optical fiber in the second optical fiber ribbon 710. Then the end surfaces are moved in the same direction, as indicated by the arrows of FIG. 7c, from the second position to a third position in which the end surfaces of all optical fibers in first optical fiber ribbon 700 are pressed against end surfaces of optical fibers in the second optical fiber 710. Then, as shown in FIG. 7d, opposite fiber ends will deform, mostly elastically, allowing this contact between all opposite fibers, this step being said to produce an overlap. The end surfaces are maintained in the third position during a first time period. The ends of the optical fibers in the first 700 and second 710 optical fiber ribbon are during the movement between the first and third positions maintained at a first temperature and during the first time period at a second temperature equal to or higher than the first temperature. The first and second temperatures are selected to be sufficiently high in order that the material of the ends of the optical fibers will soften, so that the ends of the optical fibers can be somewhat deformed in the pressing operation of the end surfaces against each other, but not being sufficiently high in order that a melting or fusing of the ends or a joining of the ends of opposite optical fibers in the first and second optical fiber ribbons will take place. The first period, during which the end surfaces are pressed against each other, is taken to be so long as to achieve such deforming of the ends of opposite optical fibers, that elastic stresses in all pairs of opposite end surfaces of the optical fibers are substantially relieved or relaxed. This is particularly important for the fiber pairs, the end surfaces of which at the beginning of the pressing operation have first contacted each other and which thus have been most deformed in the pressing operation between the second and third positions.

During a second time period subsequent to the first time period the heating of the ends of the optical fibers is continued at a third temperature higher than the first and second temperatures. The third temperature is selected to be so high that a melting and thereby a joining of opposite ends of the optical fibers takes place and the length of the second time period is selected accordingly to allow the melting and joining. Owing to the previous relaxing of elastic stresses and strains the ends will during this fusioning step be minimally deformed and in particular the cores of the fibers will maintain their straight configuration and a thus the loss in the splices formed will be at a minimum.

The velocity of the movement of the opposite end surfaces between the second and third positions can preferably be lower than the velocity of the movement between the first and second positions, e.g. be substantially equal to half the latter velocity.

Figure 7E:
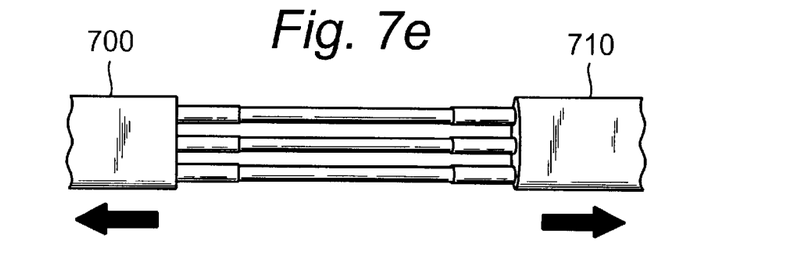

During a third time period which can be selected to coincide with an end period of the second time period or which starts when the ends of the optical fibers have been maintained at the second temperature during a predetermined time period, and as indicated by the arrows in FIG. 7e, the ends of opposite optical fibers can be pulled away from each other through a predetermined, short distance in order to straighten the deformed fiber ends a little. This short distance can be a little smaller than the distance used for producing the overlap, e.g. be 0.5–0.9 thereof. The velocity of the movement between the second and third positions can then be substantially equal to velocity of the movement used when the end surfaces are pulled away from each other.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

A complete understanding of the invention and of the above and other features thereof may be gained from a consideration of the following detailed description of non-limiting embodiments presented hereinbelow with reference to the accompanying drawings, in which.

DETAILED DESCRIPTION

All materials emit light, i.e. electromagnetic radiation of visible wavelengths, when they become sufficiently hot. The colour or wavelength and intensity of emitted light depend on the temperature of the object. A change of the temperature of a material thus changes the colour and the intensity of the material. For example an iron wire first glows with a dull red colour, when it is heated from ambient temperature, and then changes its colour to orange-red when the temperature is further increased. Solid and liquid substances emit continuous visible spectra having large widths.

All substances also absorb radiation. A body which completely absorbs radiation of all wavelengths is called an ideal black body. A corresponding condition applies for radiation of light. An ideal black body emits light with a spectrum and with an intensity, which depend only on the temperature of the body.

Figure 1:
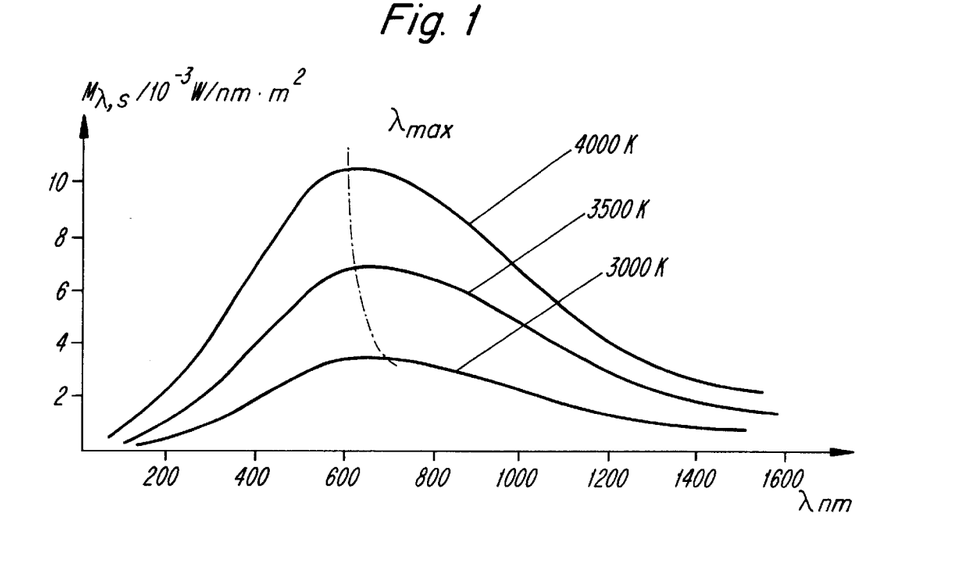
FIG. 1 is diagram of exitance (emissivity or emittance per unit area and wavelength unit) for different temperatures from a black body according to Planck's radiation law.

The correlation between emitted radiation or more exactly the emissivity or emittance as a function of the absolute temperature T and the wavelength $\lambda$ for ideal black bodies is given by Planck's radiation law $$M_{\lambda,s} d\lambda = \frac{2\pi h c_0^2 d\lambda}{\lambda^5 (e^{hc\eta/\lambda k_B T} - 1)}$$

where h is Planck's constant, $c_0$ is the light velocity in vacuum and $k_B$ is Boltzmann's constant. $M_{\lambda,s} d_\lambda$ is the intensity of emitted radiation per unit area and unit wavelength, also called exitance. FIG. 1 illustrates this relation for some temperatures. Observe the change of intensity and the displacement of the curves towards shorter wavelengths for higher temperatures.

Planck's radiation law can be employed for controlling the temperature of optical fibers in a welding process when they are spliced to each other. The quartz glass used in most optical fibers for communication, which is more or less pure silicon dioxide $SiO_2$, does not behave like an ideal black body and does not emit all wavelengths in the spectrum according to FIG. 1. However, spectral measurements of the light emitted by hot optical fibers present light emission curves, which have some general characteristics in common with the ideal spectrum curve of FIG. 1. Thus, the light emission curves of optical fibers have their maximum values displaced towards shorter wavelengths and generally have a narrower spectrum, when the temperature increases, see the diagram in FIG. 2.

The colour and intensity changes of light emitted by hot optical fibers within a limited wavelength interval depending on changes of the temperatures thereof are considerable and can be detected by means of a CCD-camera. For example the CCD-camera, which is arranged in commercially available, more or less automatic fiber welding devices, can be used for this purpose. In a black and white CCD-camera, the colour and intensity of light emitted by hot optical fibers are converted to corresponding electrical signals. A picture comprising grey scales illustrating the captured light colour and intensity is obtained, when the electrical signals are displayed on a monitor, which is also arranged in conventional automatic fiber welding devices. Thus such a picture of hot fibers showing grey scales contains information on the varying temperatures of the depicted optical fibers.

However, this information, from which the temperature of hot optical fibers can be derived, can only be used, if the light signal arriving to the camera is detected in a regular way. It means, that for comparing the temperature shown by grey scales in pictures the settings of the camera are not allowed to be changed between different captured pictures. Many commercially available camera units including CCD-elements have for example built-in electronic circuits which all the time keep the obtained picture within the dynamic range of the light sensitive CCD-elements. This is accomplished by an automatic change of the electronic gain of the camera and/or by a change of the electronic exposing time thereof Such electronic control circuits are called "Automatic Gain Control" (AGC).

However, by arranging a fixed setting of the amplification of the CCD-camera (its "Gain") and the exposing time in a procedure for measuring temperature from pictures captured of optical fibers, which can for example be used when welding to fibers to each other, the direct relation between the intensities, i.e. the grey scales, in the different portions of the camera picture and the colour and intensity of radiation of light from the optical fibers is maintained. This can in particular be used for estimating the light from heated ends of optical fibers when they are being welded to each other. Using digital image processing of the video signals obtained from the camera to determine the grey scales in appropriate portions of a captured image and using the values of the grey scales for feedback, an automatic control of the temperature in a welding process can be executed. It can for example be decided whether the temperature is within some desired limits, such as when welding optical fibers, whether the ends of the optical fibers have achieved a sufficiently high temperature in order to produce a splice having a sufficiently low attenuation.

Figure 2:
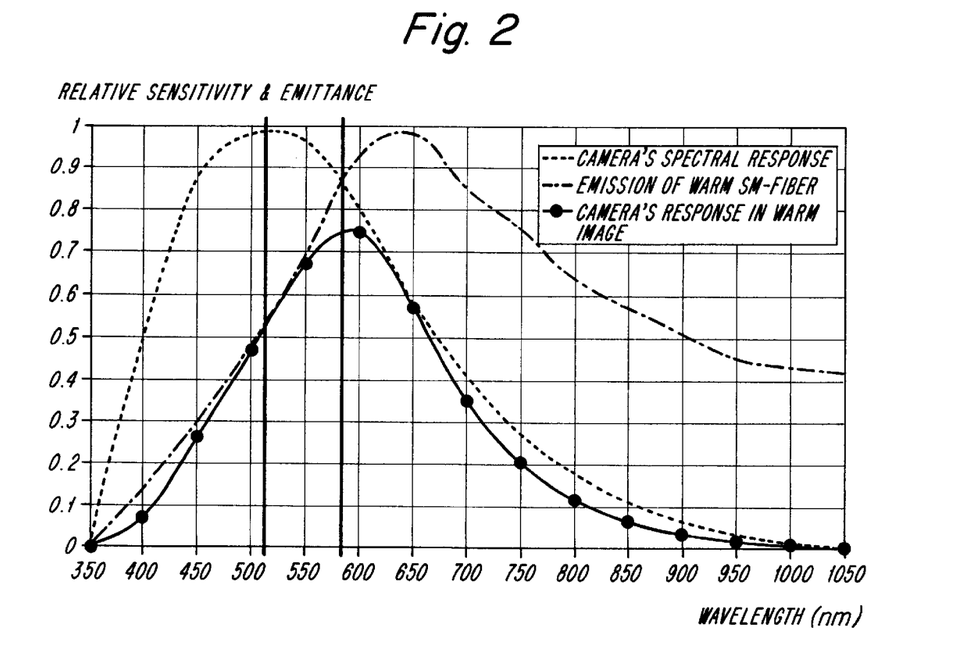
FIG. 2 is a diagram showing the spectral response of a CCD-camera together with the emission curve of a hot single-mode-fiber and the product thereof, two vertical lines showing how the optical system restricts the spectrum.

The radiation from a heated optical fiber when being welded has a measured spectrum, which is illustrated by the line of dashes and dots in the diagram in FIG. 2. The light sensitive elements of the camera have a limited spectral sensitivity, i.e. the elements are more sensitive to light of some wavelengths than to light of other wavelengths.

Furthermore, the optical system of the camera restricts the radiation spectrum, in particular in the case where it is provided with extra filters. The two vertical lines show the restriction of the spectrum because of the optical system. The area below the solid line curve in FIG. 2 shows that portion of the light intensity emitted from a hot optical quartz fiber, which is converted to video signals in the light sensitive part, the CCD-array, of the camera, for normal fiber temperatures. An increase of the temperature of the optical fibers results in elevating the emission curve as a function of wavelengths and displacing the emission curve to the left, which appears as an increase of the corresponding light intensity in a picture of the optical fibers.

Figure 3:
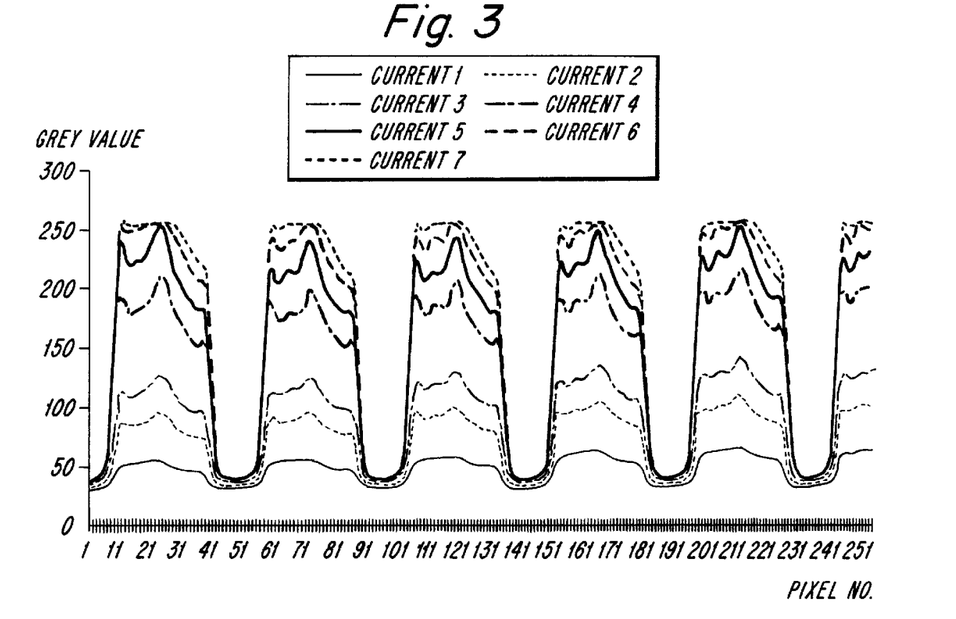
FIG. 3 is a diagram of intensity profiles obtained in pictures of fibers, which are heated in an electric arc for different electrode currents in a welding device for fiber ribbons, as a function of the position in a direction perpendicular to the longitudinal direction of the fibers.

As observed above, the temperature control of the hot place used in welding optical fibers to each other requires a fixedly set camera control. The light intensities as seen in different pictures are a direct function of the colour and intensity of emitted light and thus on a welding current flowing between welding electrodes only in the case where the AGC of the camera does not influence the signal captured by the light sensitive elements of the camera. The diagram in FIG. 3 shows the intensity profiles for hot fibers for a plurality of different, such welding currents and thus also for different temperatures as obtained in a welding device for optical fiber ribbons. In this diagram the measured curves correspond to light intensities captured along lines in different pictures, which lines extend perpendicularly to the longitudinal direction of the optical fibers, as seen in the pictures. The curve or profile called "Current1" indicates a low heating of the fibers corresponding to a few grey scales in the picture. The profiles at "Current6" and "Current7" indicate high temperatures, for which an over-amplification of the camera has taken place and the built-in automatic setting system of the camera has come into operation in order to maintain the dynamic of the obtained picture.

Figure 6:
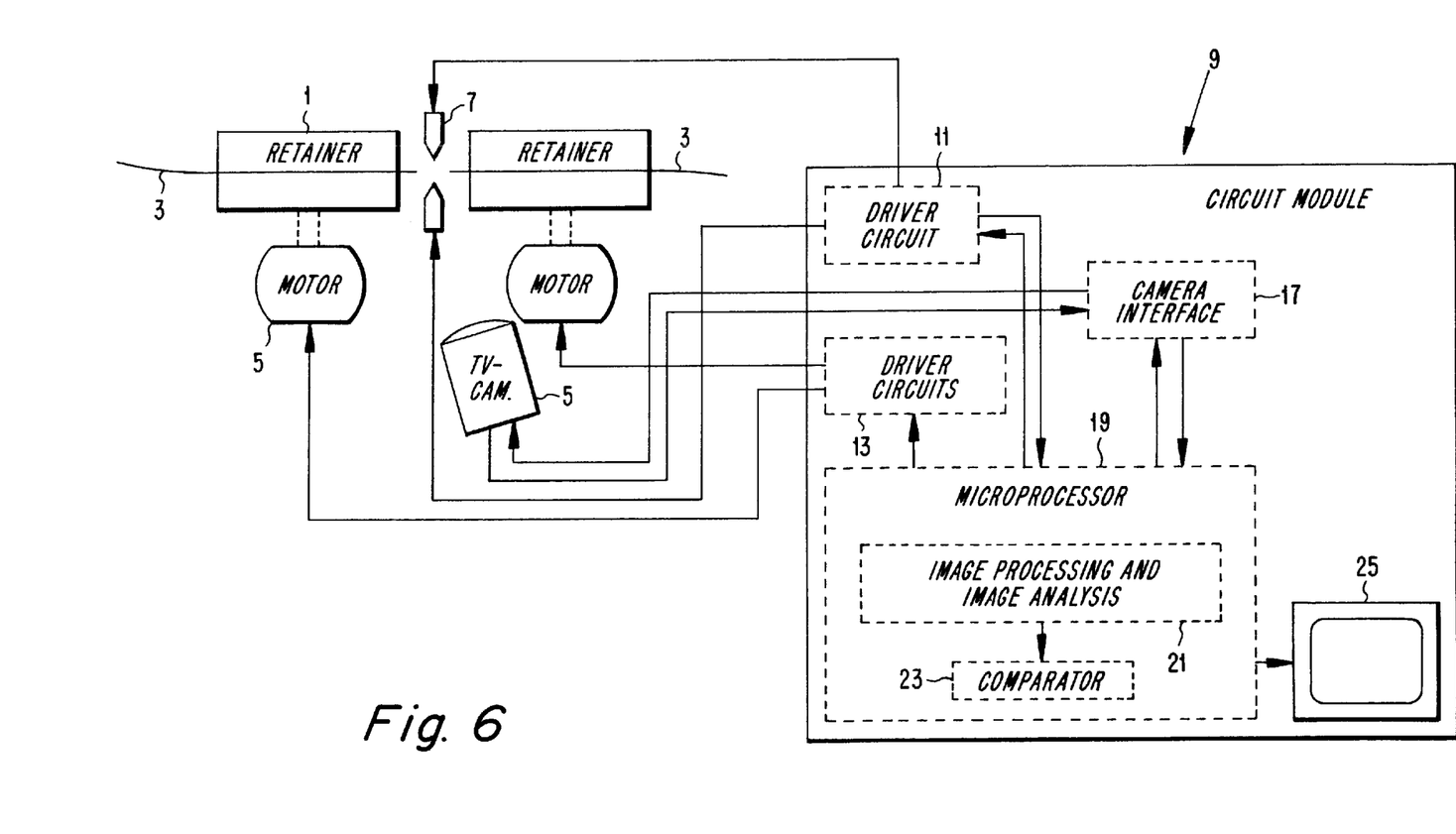
FIG. 6 is a schematic picture of the mechanic and electronic components of an automatic fiber welding device.

The correlation discussed above between measured light intensity and temperature of an optical fiber can be used in a fiber welding device of the automatic type, which is schematically shown in FIG. 6. This device has clamps 1, in which end portions of optical fibers assembled to optical fiber ribbons 3 are placed and retained during adjusting their position and in the welding process. The clamps 1 are displaceable in a direction parallel to the longitudinal direction of the fibers. Possibly, the clamps 1 can also be displaceable in directions perpendicular to the fiber longitudinal direction in order to align the fibers with each other. Generally, however this alignment is produced by placing the fiber ends in V-grooves or similar fixed mechanical guides. The clamps 1 are operated along suitable mechanical guides, not shown, by means of control motors 5. Electrical lines to electrodes 7 and to the motors 5 extend from an electronic circuit module 9, from associated driver circuits 11 and 13 respectively arranged therein. From the CCD-camera 15, which is provided with an optical filter, not shown, for selecting wavelengths, which are suitable in particularly light intensity determinations, from which temperature calculations are then made, an electronic line is arranged to a camera interface 17 in the electronic circuit module 9, from which lines extend to a control unit 19, suitably a microprocessor. In particular, a video signal is provided to an image processing and image analysing program module of the microprocessor 19. It performs image processing in order to determine among other things the positions of the fiber ends and in order to determine the light intensity in selected areas in captured pictures as will be described in detail hereinafter.

A comparator module 23 is connected to the image processing and image analysing unit 21 in order to compare the determined light intensity to different set values stored in some memory, not shown. Pictures obtained from the camera 15 and the microprocessor 19 and in particular the image processing and image analysing program 21 thereof can be displayed on a monitor 25. The different steps in the procedure are controlled by the microprocessor 19. It performs the above mentioned steps of the procedure and thus controls the displacement of the fiber ends in relation to each other by energizing the motors 5 depending on an image processing signal received from the image processing and image analysing module 21 and provides the image processing and image analysing module with a signal for starting an analysis of an obtained image and a determination of the positions of the light intensity of the fiber ends in the captured image. Furthermore, the microprocessor 19 controls the time, when a heating of the fiber ends is to be made, by energizing the driver circuit 11 to provide the welding electrodes 7 with an electric voltage, so that a suitable electrode current flows between the electrodes, and it also controls those time periods, during which different electrode currents are to be supplied.

Figure 4:
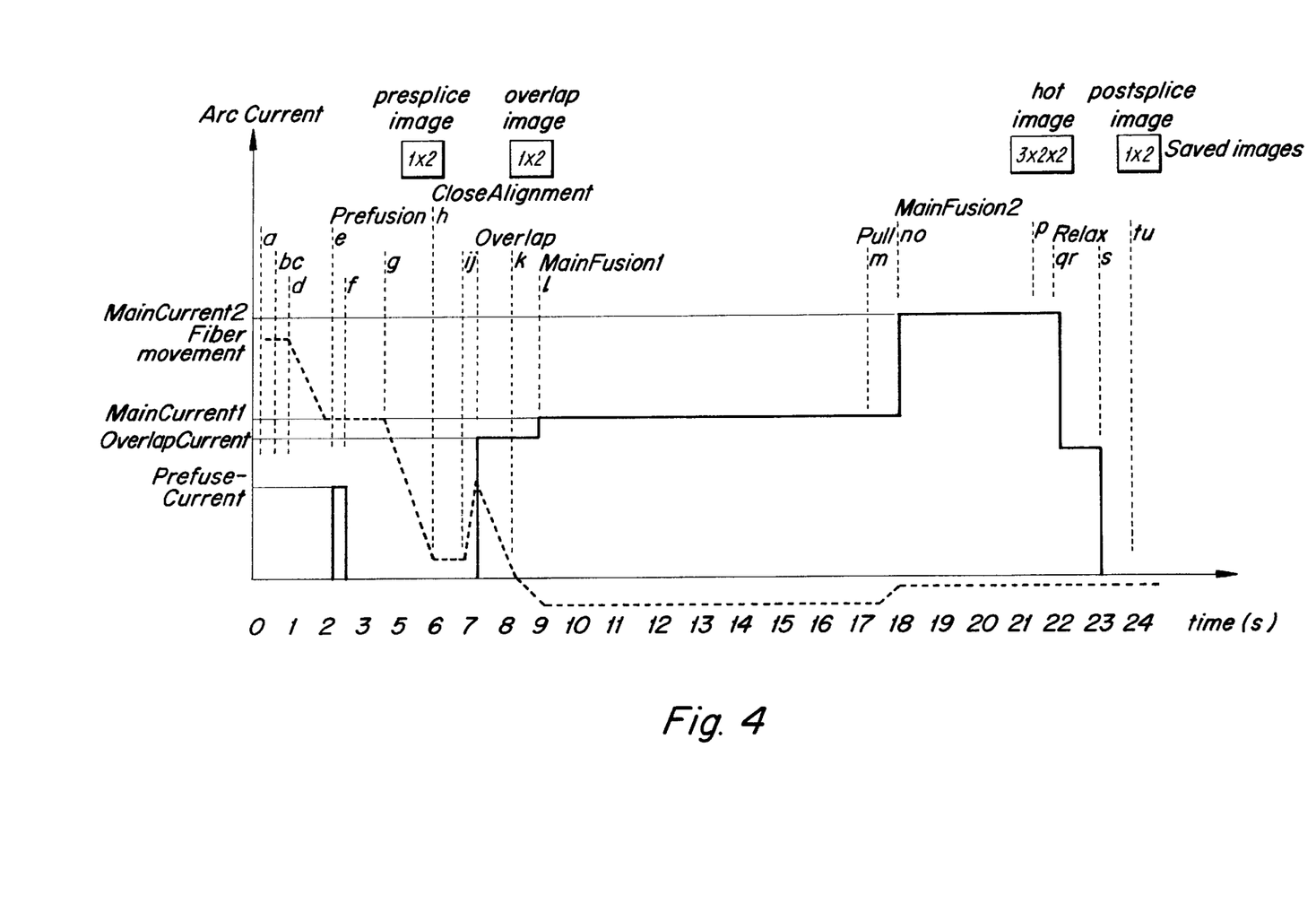
FIG. 4 is a diagram illustrating the welding sequence in a 12-ribbon welding device comprising curves of electrode current and displacements as functions of time.

A method of welding two optical fiber ribbons to each other will now be described with reference to the diagram in FIG. 4, which at the [dotted] solid line shows the current, which flows between the electrodes 7, thus the electrode current, as a function of time, and which at the dotted [solid] line shows the distance of the fiber ends from each other as a function of time. The procedure starts from the state when the end surfaces of the fibers are opposite each other and are located at a distance from each other and then move closer and closer to each other, see the times a, b, c, d in FIG. 4. At time periods starting at the times a, b, c the camera settings are optimized, all fibers in the picture are identified by the image processing and analysing module and their positions are thereby roughly determined and a welding program is selected respectively. In the time period starting at the time d the fiber ends are moved to a small distance of each other, which happens at time e. Then during a short time period, a preparatory heating of the optical fiber ends is performed, starting at the time c or "Prefusion" and ending at the time f, to a low temperature corresponding to a low electrode current "PrefuseCurrent" used for a preparatory cleaning and a small rounding of the fiber ends. Then the fiber ends are moved closer and closer to each other from the time g until they nearly touch each other at the time h or "CloseAlignment".

Then the fiber ends are moved away from each other through a small predetermined distance in the time interval between the times i and j, in order to then, at the time j or "Overlap", start the very welding by supplying a suitable high voltage to the welding electrodes. During all of the previous procedure the automatic setting system of the CCD-camera has been active, but it is shut off now soon before the time j or "Overlap", so that the CCD-camera can work from now on as a measuring detector.

The value of the integration time IT of the camera and the GC-value (the electronic gain of the camera, the "Gain Control") of the camera are set to fixed values IT_MF1 and GC_MF1 respectively. These values are predefined and have been determined from the calibration value of the optical system/CCD determined when manufacturing/adjusting the welding device. By means of these preset values IT_MF1 and GC_MF1 and for the present fiber type a current intensity "MainCurrent1" has been calculated or determined, which is to be used in the softening period of the welding procedure, which starts at a time "MainFusion1", the calculating or determining being made by process technicians and/or by means of the procedure "Current Test" described hereinbelow. The current intensity "MainCurrent1" is set, so that it gives a correct temperature in the fibers during this stage and also gives a clear image of the heated fiber ends on the display monitor.

The fiber ends are moved from the position in the state j at some predetermined distance from each other slowly in a direction towards each other and a considerable current "OverlapCurrent" is allowed to flow between the electrodes 7, the fiber ends then approaching each other and contacting each other and being pressed to each other. This process is performed during a time period "OverlapTime", which is longer than 1 second, and the movement velocity is made smaller after the time k, at which the first or at least some fiber ends come in contact with each other. Most frequently the individual fibers in a fiber ribbon have different lengths, i.e. the end surfaces of the individual fibers are not located in a plane perpendicular to the longitudinal direction of the fiber ribbon. When for example cutting off fiber ribbons they cannot often be cut off completely perpendicularly to the longitudinal direction of the fiber ribbon. Also, a stripping operation required to strip the polymer coatings of the fibers of an optical fiber ribbon can impose strains on the fibers in a fiber ribbon, which fibers then return or relax differently after the stripping operation. Though a contact thus exists between at least two opposite fibers at the time k, it is not certain that the other fibers in the fiber ribbon then have contact with opposite fibers. Their end surfaces can instead be located at a small distance of each other. This distance can comprise as much as about 10–15 $\mu$m for fiber ribbons containing twelve parallel fibers.

When the fiber ends are sufficiently pressed to each other, so that substantially all end surfaces of opposite fibers touch each other, which is obtained at a time 1 or "MainFusion1" mentioned above, they are maintained in this position and then the temperature of the fiber ends is increased by being heated in the electric arc between the electrodes by means of the somewhat higher electrode current "MainCurrent1", as already mentioned, to a temperature, which is sufficient to make that the fiber ends soften but which is lower than the temperature, at which the final welding will be made and at which the material in the fiber ends is fusioned together. The softening period, which starts at 1 or "MainFusion1," has a long duration, such as of the magnitude of order 5–15 s and in particular it can be between 8 and 10 s.

The long softening period at a temperature lower than the welding temperature is required in order to obtain such deforming of the ends of opposite optical fibers, that elastic stresses in all pairs of opposite ends of the optical fibers are substantially relieved or relaxed. This is most important for ends of opposite optical fibers, the end surfaces of which at the beginning of the pressing operation, at the time k, have first come in contact with each other and which thus have been much deformed in the pressing operation for the overlap.

The temperature set during the softening period is also so low, that the risk that fiber ends, which in the beginning of a period lack contact with an opposite fiber end, will get a "match" like look having shapes similar to a ball is small. During all of the steps, which start at the times "Overlap" and "MainFusion1", all that happens at the fiber ends is well visible on the display monitor using the fixed setting of the control of the CCD-camera.

During all these time periods also the captured images are automatically analyzed by the image processing and image analysing program 21 of the device. The temperature of the fiber ends is determined according to the method described above by evaluating light intensities in the picture, i.e. by evaluating the grey scales. It can be made by measuring in the picture along lines, which are perpendicular to the longitudinal direction of fiber ribbons in the picture, and which are located close to the picture of the very end surfaces, compare the diagram in FIG. 3, and by determining the light intensity of those portions in the picture, which correspond to each fiber. In particular, the intensity can be determined in those portions, which correspond to the central parts of each fiber end, for example over a predetermined, centrally located distance corresponding to less than half the diameter of the fibers. The average of the determined intensity values is calculated and compared to a predetermined set value, see hereinbelow. If the average deviates too much from the set value and thus the temperature is not the intended one, a signal thereof is indicated to the operator, for example as a message on the monitor, such as "Temperature setting incorrect. Run Current Test and repeat the splicing procedure", or the current intensity "MainCurrent1" used in the softening period is automatically increased by some predetermined small step. The latter procedure is generally substantially equivalent to increasing the temperature by some corresponding step.

The softening step is terminated at the time denoted by n, o or "MainFusion2" passing through a time m. At the time m or "Pull", which occurs a little less than 1 s before the time "MainFusion2", the ends of the fiber ribbons are pulled away somewhat from each other in order to somewhat extend the splices between individual fibers. The ends of the fiber ribbons return nearly to the positions when coming in contact at the time j. The extension of the fibers is terminated at the time "MainFusion2". Directly after this time the IT-value and GC-value of the camera are changed to other fixed values IT1__MF2 and GC1__MF2. In the same way as the previously set values IT__MF1 and GC__MF1 used in the softening stage these new values are predefined and have been determined from the calibration value of the optical system/CCD when manufacturing/adjusting the device. As above, by means of the set values IT1__MF2 and GC1__MF2 an electrode current "MainCurrent2" has also been calculated by process technicians and/or has been determined by means of the procedure "Current Test" described hereinbelow for welding the present type of fiber ribbons at the present conditions, such as the ambient pressure, electrode state, etc. The current intensity "MainCurrent2" gives as above the desired temperature in the fibers during the step, which sum at the time "MainFusion2" and furthermore a clear picture of the fibers during this step is obtained, so that also the cores of the fibers are visible.

This higher current intensity "MainCurrent2", which can be 2–15 mA higher that the current intensity "MainCurrent1", is thus used from the time n, o or "MainFusion2", during the very welding stage, which has a duration of a few seconds, typically 2–4 s, and during which the fusioning of the fiber ends to each other takes place. The temperature determined by the electrode current "MainCurrent2" is so high, that the surface tension forces of the fiber materials overcome all other forces acting on the splice, such as internal viscous forces, radial forces, bending forces, etc., of the material. Thereby an alignment of the fibers with each other is produced and homogenous splices are formed between opposite fibers in the two fiber ribbons. During the very last part of the welding stage comprising the high current "MainCurrent2", at the time denoted p or "HotImage", several, e.g. three, pictures are captured for estimating the attenuation in the produced splices. The pictures show the cores and in particular the lateral displacements or offsets of the cores and from them the attenuation can be calculated in a known way.

As has been described above for the time periods starting at "Overlap" and "MainFusion1", also during the very welding stage starting at "MainFusion2" the captured image is automatically analyzed by the image processing and image analysing program module 21 of the device and the temperature of the fiber ends is determined. If the determined temperature average deviates too much from the desired value, as above a signal thereof is indicated to the operator or the current intensity used in this step is automatically increased, as outlined above. During all of this stage also the region at the fiber ends is well visible on the monitor 25, so that an operator can directly see what actually happens, how the fiber ends are deformed and are molten to each other and how possible lateral deviations are reduced owing to the surface tension.

At the time q, r or "Relax", the electrode current is reduced to a considerably lower value to have this value during some second in order to then completely stop at the time s. During this time period after the time "Relax" the fibers are thus allowed to gradually cool. After a period of about 1 s after the stop of the electrode current at s, pictures are captured of the finished splice at a time t, u and the loss in the splices is calculated. Thereupon the spliced fiber ribbons can be detached from the clamps 1 and removed from the device.

In an automatic determination of welding currents, here called "Current Test", an automatic function for determining the two current intensities "MainCurrent1" and "MainCurrent2" is used, which are employed in the procedure as described above. These two parameters can either be dynamic variables and be set automatically by the welding s device after performing the current test and/or be conventional welding parameters and be set manually by the user after performing the test for the current fiber in the present environment.

Figure 5:
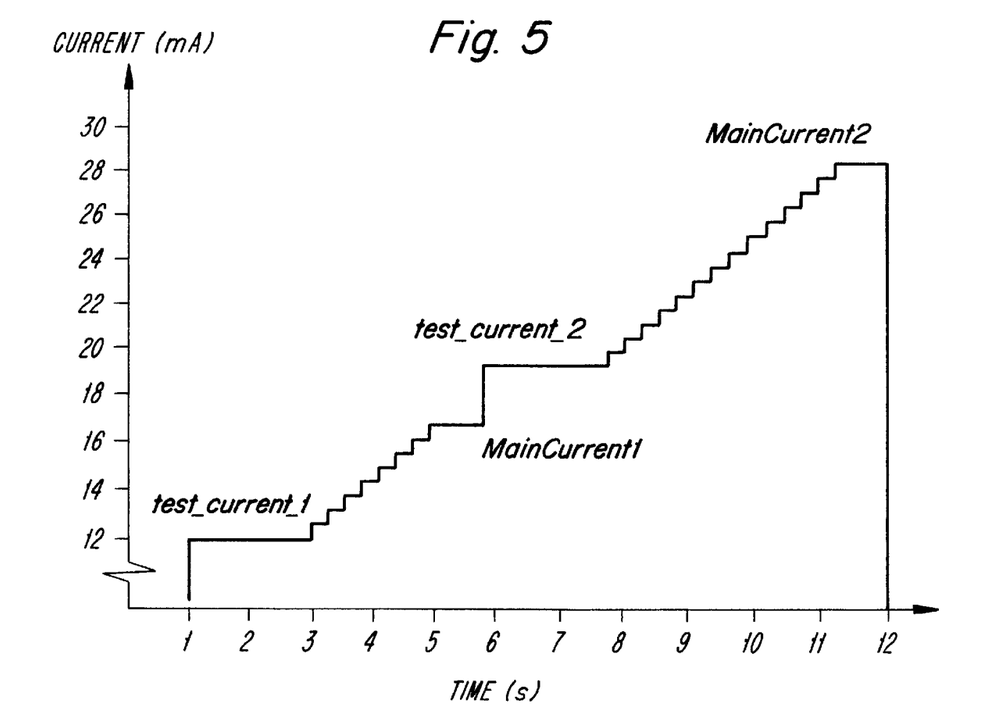
FIG. 5 is a diagram of current as a function of time in a testing routine for automatic determination of welding currents.

The procedure can according to the flow as described hereinbelow and with reference to FIG. 5 comprise the following steps:

a. an optical fiber ribbon, which has a long stripped and cleaned end portion, is placed in the retainers 1 and in guide grooves of V-type, not shown, in the welding device;

b. the integration time IT and the gain GC of the camera are fixed as above to fixed values IT_MF1 and GC_MF1. These values are predefined for the camera and determined by the calibration value of the optical system/CCD when manufacturing/adjusting the welding device;

c. the electric arc between the electrodes is ignited for a low current intensity, "test_current_1" during a short period, called "test_current_duration", having a length of e.g. 200 ms;

d. a picture is captured, an actual value of the light intensity is determined therefrom in the manner described above for the end portions of the fibers and is compared to desired value, which has earlier been determined to give a suitable fiber temperature the employed type of fiber ribbon;

e. if the determined light intensity value is decided not to be sufficient and in particular deviate from the desired value by more than a small value c and thus the temperature is too low, provided that the current intensity from the beginning is lower than the value, which gives a light intensity value equal to the desired value, test_current_1 is increased by a fixed step of for example 0.5 mA.

The points c.–e. are repeated, until the actual value of the light intensity exceeds or is equal to the desired value or generally deviates from the desired value by an amount smaller than the small constant ϵ. The current intensity thus obtained or used is set to be the current intensity "MainCurrent1" which is to be used during the softening step described above.

f. the integration time and the gain of the camera are now changed to the second fixed values IT1_MF2 and GC1_MF2. These values are predefined for the camera and are determined by the calibration value of the optical system/CCD set when manufacturing/adjusting the welding device and gives a clear picture of the fiber ends at the high temperatures, which are used during the very welding or fusioning stage, in particular so that the fiber cores are visible in the picture;

g. the electric arc is now produced using a higher current called "test_current_2", which is higher than the first determined current value "MainCurrent1", and it is allowed to last during only a short period, "test_current_duration", having a time length of e.g. 200 ms;

h. a picture is captured, an actual value of the light intensity of the picture of the fiber ends is determined as above and is compared to a set value, which is preset in order to accomplish the correct, desired welding temperature in the welding stage;

i. if the determined light intensity value is not sufficient and the temperature thus is too low or generally the determined actual value deviates from the set value by more than a small constant c, as above the electrode current is increased by a step of for example 0.5 mA as above.

The points g.–j. are repeated until the determined actual value of the light intensity is higher than or is equal to the now used desired value or generally deviates from desired value by less than the small value ϵ. The current intensity "MainCurrent2" searched for is set equal to the value of the current value then used.

The current intensities "MainCurrent1" and "MainCurrent2" determined by means of this procedure are presented on the display monitor to be manually fed into the welding device or to be automatically fed as dynamic variables directly into the control program in the microprocessor 19 of the welding device.

Thus, advantageous methods have been described for achieving high quality splice between optical fibers, in particular between optical fibers assembled to ribbons, using only components which already are available in commercial automatic fiber welding devices.

Additional advantages and modifications will readily occur to those skilled in the art. Therefore, the invention in its broader aspects is not limited to the specific details representative devices and illustrated examples shown and described herein. Accordingly various modifications may be made without departing from the spirit or scope of the general inventive concept as defined by the appended claims and their equivalents.

What is claimed is:

1. A device for welding a first optical fiber ribbon to a second optical fiber ribbon, the first and second optical fiber ribbons comprising each a plurality of optical fibers, in the welding operation ends of optical fibers in the first optical fiber ribbon being welded to ends of optical fibers in the second optical fiber ribbon, the device comprising:

electrodes connected to a high-voltage source for forming an electric arc, in which the ends of the optical fibers are heated when an electrode current passes between the electrodes, retainer and positioning means for placing the optical fibers, so that an end surface of an optical fiber in the first optical fiber ribbon is located opposite and at an end surface of an optical fiber in the second optical fiber ribbon, and a microprocessor connected to the high voltage source and to the retainer and positioning means, the microprocessor being arranged to control the retainer and positioning means, so that the end surfaces are made to move toward each other from a first position at a small distance of each other to a second position in which an end surface of at least one optical fiber in the first optical fiber ribbon is in contact with an end surface of an optical fiber in the second optical fiber and then to a third position in which the end surfaces of all optical fibers in the first optical fiber ribbon are pressed against end surfaces of optical fibers in the second fiber ribbon with an overlap, and to maintain the end surfaces in the third position during a first time period, and to control the high voltage source to make such electrode currents pass between the electrodes that the ends of the optical fibers during the movement between the first and third positions are maintained at a first temperature during the first time period and at a second temperature equal to or higher than the first temperature during a second time period, the first and second temperatures being sufficiently high in order that the material of the ends of the optical fibers will soften, so that the ends of the optical fibers can be somewhat deformed at the pressing operation of the end surfaces against each other, but not being sufficiently high in order that a melting of or a joining of the ends of opposite optical fibers will take place, and to control the retainer and positioning means to make the first period, during which the end surfaces are being pressed against each other, have such a length as to achieve such deforming of the ends, that elastic stresses in all pairs of opposite end surfaces of the optical fibers are substantially relieved or relaxed, and wherein the microprocessor being arranged to control the high voltage source, so that the heating of the ends of the optical fibers being then continued at a high temperature, at which a melting and thereby a joining of ends of opposite optical fibers in the first and second optical fiber ribbons takes place.

2. The device of claim 1, wherein the microprocessor is arranged to control the retainer and positioning means to move the end surfaces between the second and third positions with a velocity of the movement lower than a velocity of the movement between the first and second positions.

3. The device of claim 2, wherein the microprocessor is arranged to control the retainer and positioning means to move the end surfaces between the second and third positions with a velocity of the movement substantially equal to half the velocity of the movement between the first and second positions.

4. The device of claim 1, wherein the microprocessor is arranged to control the retainer and positioning means to pull, during a third time period at an end of the second time period or when the ends of the optical fibers have been maintained at the second temperature during a predetermined time period, the ends of opposite optical fibers away from each other through a predetermined, short distance.

5. The device of claim 4, wherein the microprocessor is arranged to control the retainer and-positioning means to move the end surfaces so that the velocity of the movement between the second and third positions is substantially equal to a velocity of the movement used when the end surfaces are pulled away from each other.

* * * * *